US006702819B2

(12) United States Patent
Lechot

(10) Patent No.: US 6,702,819 B2
(45) Date of Patent: Mar. 9, 2004

(54) SURGICAL REAMER

(75) Inventor: André Lechot, Orvin (CH)

(73) Assignee: Precimed S.A., Orvin (CH)

( * ) Notice: Subject to any disclaimer, the term of this patent is extended or adjusted under 35 U.S.C. 154(b) by 0 days.

(21) Appl. No.: 09/898,542

(22) Filed: Jul. 2, 2001

(65) Prior Publication Data

US 2002/0010470 A1 Jan. 24, 2002

(30) Foreign Application Priority Data

Jul. 20, 2000 (CH) ............................................. 1435/00

(51) Int. Cl.$^7$ ............................ A61B 17/16; B23D 77/00
(52) U.S. Cl. ........................................ 606/80; 408/227
(58) Field of Search ............................. 606/79, 80, 81, 606/180; 408/227

(56) References Cited

U.S. PATENT DOCUMENTS

| | | | | |
|---|---|---|---|---|
| 4,023,572 A | * | 5/1977 | Weigand et al. | 606/81 |
| 4,811,632 A | * | 3/1989 | Salyer | |
| 5,658,290 A | * | 8/1997 | Lechot | 606/80 |
| 6,129,732 A | * | 10/2000 | Lechot | 606/80 |
| 6,283,972 B1 | * | 9/2001 | Riley | 606/81 |

* cited by examiner

Primary Examiner—Jeffrey A. Smith
(74) Attorney, Agent, or Firm—Bugnion S.A.; John Moetteli

(57) ABSTRACT

A reamer intended for surgery, made up of a hollow body of revolution provided with four radial arms which are perpendicular to each other so as to form a cross for fixing the reamer on a reamer holder. The cross formed by the radial arms is made up of a first diametral bar (1), a pin (2) passing through the first bar at its center and protruding each side of this bar, and two radial bars (3, 4) which have an axial hole via which each of these radial bars is engaged on the pin.

With this construction, which is simple to produce, it is possible to omit welds and to eliminate the cleaning problems inherent to these welds.

1 Claim, 1 Drawing Sheet

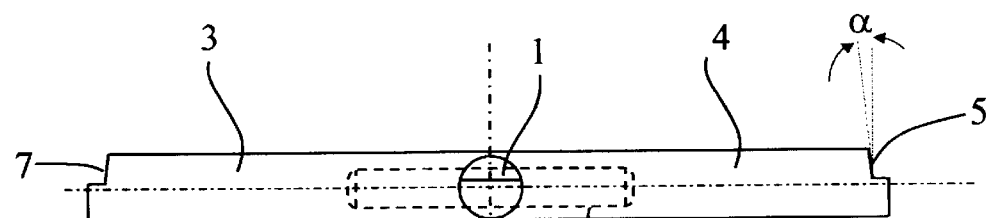
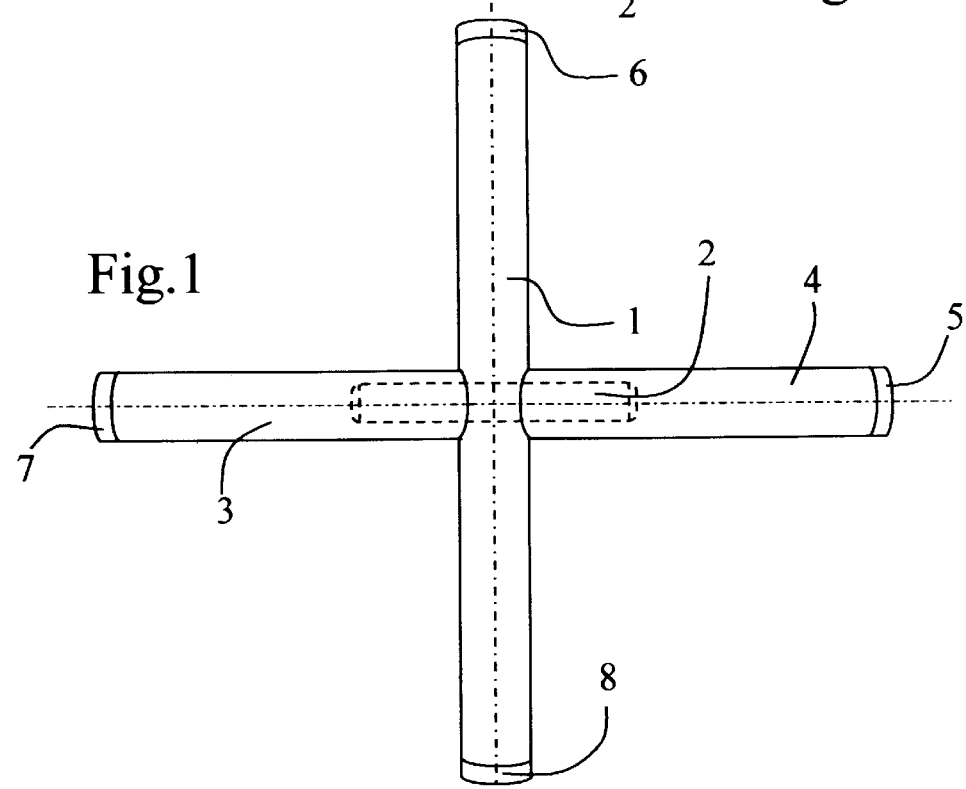
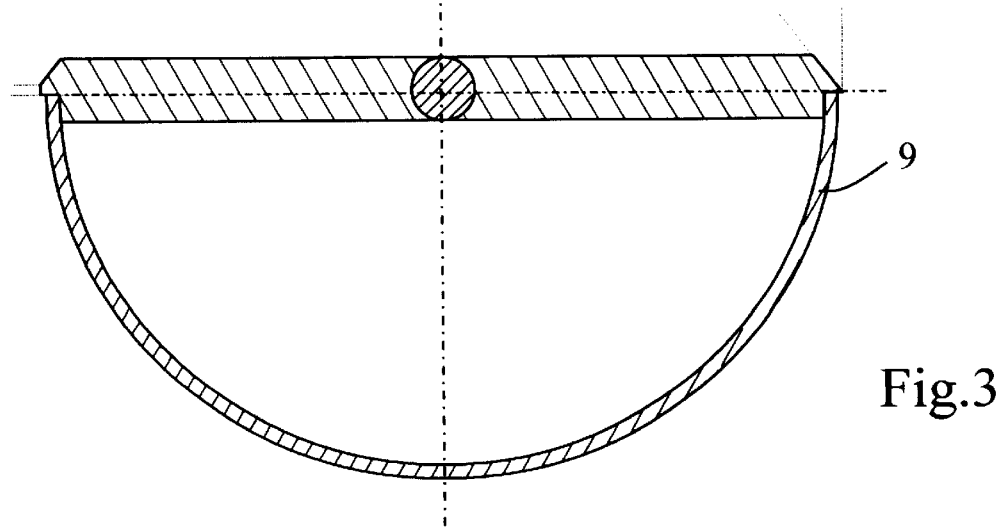

SURGICAL REAMER

BACKGROUND OF THE INVENTION

The invention relates to a reamer intended for surgery, made up of a hollow body of revolution provided with four radial arms which are perpendicular to each other so as to form a cross for fixing the reamer on a reamer holder.

PRIOR ART

A reamer of this kind is described and illustrated in patents EP 0,704,191 and U.S. Pat. No. 5,658,290. The presence of four arms allows for centered and stable fixation of reamers of different diameters on the reamer holder described in these same patents. The arms have hitherto been fixed to each other by conventional welding, that is to say adding material. However, a blackening of the weld has been observed upon sterilization of the reamer. Such blackening is unacceptable for a surgical instrument. In addition, the weld has a certain porosity which poses a problem when cleaning the instrument.

These disadvantages could be eliminated by using a laser weld, that is to say without adding material. However, such a weld requires precise and expensive preliminary machining of the parts to be assembled. Thus, a solution of this kind must be set aside for reasons of economy.

SUMMARY OF THE INVENTION

It is an object of the present invention to permit assembly of the cross without welding and by using means which are economical and easy to implement.

The reamer according to the invention is distinguished by the fact that the cross formed by the radial arms is made up of a first diametral bar, a pin passing through the first bar at its center and protruding each side of this first bar, and two radial bars which have an axial hole via which each of these bars is engaged on the pin.

The pin is an inexpensive element. The axial holes are easy to form and said engagement is an easy and straightforward operation. The fixation obtained is very stable.

BRIEF DESCRIPTION OF THE DRAWINGS

The attached drawing shows by way of example an embodiment of the invention.

FIG. 1 is a plan view of the cross for fixing the reamer.

FIG. 2 is a view of this fixing cross on the axis of the diametral bar.

FIG. 3 is a cross section through the reamer on a plane of symmetry perpendicular to the diametral bar of the cross.

DESCRIPTION OF THE PREFERRED EMBODIMENTS

The fixing cross shown in FIGS. 1 and 2 is made up of a diametral bar 1 with a hole bored perpendicular to its axis, in which hole there is fitted a cylindrical pin 2 whose length is such that it protrudes greatly on each side of the bar 1. Two radial arms 3 and 4 perpendicular to the bar 1 are engaged on this pin, on each side of the bar 1. For this purpose, the arms 3 and 4 are provided with a blind axial hole whose diameter is slightly less than the diameter of the pin 2.

At the ends of the arms of the cross thus formed, truncated facets 5, 6, 7, 8 are machined on part of the diameter of these arms, said truncated facets 5, 6, 7, 8 being situated on one and the same conical surface whose axis passes through the center of the fixing cross. The diameter of this conical surface in the area of the facets 5 to 8 corresponds to the internal diameter of the reamer 9 shown in FIG. 3, measured in its equatorial plane, in such a way that the fixing cross can be adjusted in the hemispherical cap of the reamer 9 as is shown in FIG. 3. The cross is fixed to the reamer 9 by laser welding. The ends of the fixing cross are additionally beveled, as can also be seen in FIG. 3.

In FIG. 3 the reamer has been shown diagrammatically as a simple smooth cap, but in reality this cap is of course provided with teeth, as is shown for example in U.S. Pat. No. 4,811,632.

The reamer can of course have a shape other than hemispherical, for example a conical shape.

What is claimed:

1. A reamer intended for surgery, made up of a hollow body of revolution provided with four radial arms which are connected to the body of revolution and are perpendicular to each other so as to form a cross for fixing the reamer on a reamer holder, wherein the cross, formed by the radial arms, is made up of a first diametral bar (1), a pin (2) passing through the first bar at its center and protruding through each side of this bar, and two radial bars (3, 4) which have an axial hole via which each of these radial bars is engaged on the pin.

* * * * *

UNITED STATES PATENT AND TRADEMARK OFFICE
CERTIFICATE OF CORRECTION

| | | |
|---|---|---|
| PATENT NO. | : 6,702,819 B2 | |
| APPLICATION NO. | : 09/898542 | |
| DATED | : March 9, 2004 | |
| INVENTOR(S) | : Lechot | |

It is certified that error appears in the above-identified patent and that said Letters Patent is hereby corrected as shown below:

Column 1 after the title on line 1, insert the following header and paragraph:

-- CROSS REFERENCE TO RELATED APPLICATIONS
This application claims priority to Switzerland Application No. 1435/00, filed July 20, 2000. --

Signed and Sealed this

Thirteenth Day of November, 2012

David J. Kappos
*Director of the United States Patent and Trademark Office*